United States Patent
Braeunling et al.

(10) Patent No.: US 10,128,539 B2
(45) Date of Patent: Nov. 13, 2018

(54) CYCLIC PHOSPHONAMIDES AS AN ELECTROLYTE COMPONENT FOR LITHIUM-ION BATTERIES

(71) Applicant: Wacker Chemie AG, Munich (DE)

(72) Inventors: Daniel Braeunling, Munich (DE); Frank Deubel, Munich (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/527,126

(22) PCT Filed: Sep. 8, 2016

(86) PCT No.: PCT/EP2016/071165
§ 371 (c)(1),
(2) Date: May 16, 2017

(87) PCT Pub. No.: WO2017/055049
PCT Pub. Date: Apr. 6, 2017

(65) Prior Publication Data
US 2017/0365879 A1   Dec. 21, 2017

(30) Foreign Application Priority Data
Sep. 28, 2015   (DE) .................. 10 2015 218 653

(51) Int. Cl.

| | |
|---|---|
| *H01M 10/0567* | (2010.01) |
| *H01M 10/0568* | (2010.01) |
| *H01M 10/0569* | (2010.01) |
| *H01M 10/0525* | (2010.01) |
| *H01M 10/052* | (2010.01) |
| *H01M 4/134* | (2010.01) |
| *C07F 9/6584* | (2006.01) |
| *H01G 11/64* | (2013.01) |
| *H01G 11/62* | (2013.01) |
| *C07F 7/08* | (2006.01) |

(52) U.S. Cl.
CPC ....... *H01M 10/0567* (2013.01); *C07F 7/0803* (2013.01); *C07F 9/65848* (2013.01); *H01G 11/62* (2013.01); *H01G 11/64* (2013.01); *H01M 4/134* (2013.01); *H01M 10/052* (2013.01); *H01M 10/0525* (2013.01); *H01M 10/0568* (2013.01); *H01M 10/0569* (2013.01); *H01M 2300/0028* (2013.01)

(58) Field of Classification Search
None
See application file for complete search history.

(56) References Cited

U.S. PATENT DOCUMENTS

| | | | |
|---|---|---|---|
| 7,476,469 B2 | 1/2009 | Ota et al. | |
| 2002/0012850 A1 | 1/2002 | Schmidt | |
| 2014/0137400 A1* | 5/2014 | Cheng ............... | B23D 61/185 29/623.5 |
| 2015/0140445 A1 | 5/2015 | Aoki et al. | |
| 2016/0289247 A1 | 10/2016 | Bockholt et al. | |

FOREIGN PATENT DOCUMENTS

| | | |
|---|---|---|
| DE | 10027626 A1 | 12/2001 |
| DE | 102013224159 A1 | 5/2015 |
| WO | 2015078789 A1 | 6/2015 |

OTHER PUBLICATIONS

Kawashima, A. et al., Journal of the Electrochemical Society 2011, 158, A798-A801.
Aurbach, D. et al. Langmuir 2012, 28, 965-976.

* cited by examiner

*Primary Examiner* — Sin J Lee
(74) *Attorney, Agent, or Firm* — Brooks Kushman P.C.

(57) ABSTRACT

An electrolyte suitable for use in lithium ion batteries contains
100 parts by weight of aprotic solvent,
1 to 50 parts by weight of lithium-containing conducting salt,
4 to 50 parts by weight of vinylene carbonate, and
cyclic phosphonamide of the general formula 1

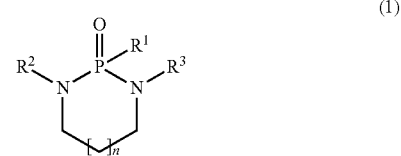

(1)

in which
$R^1, R^2, R^3$ are each hydrocarbyl which is unsubstituted or substituted by fluoro, chloro or silyl groups and which has 1-20 carbon atoms, where two or three of the radicals $R^1$, $R^2$, $R^3$ may be joined to one another, and
n has a value of 0, 1, 2, 3, 4 or 5. The electrolyte is used in a lithium-ion battery which comprises a cathode, an anode, a separator, and the electrolyte.

13 Claims, No Drawings

CYCLIC PHOSPHONAMIDES AS AN ELECTROLYTE COMPONENT FOR LITHIUM-ION BATTERIES

CROSS REFERENCE TO RELATED APPLICATIONS

This application is the U.S. National Phase of PCT Appln. No. PCT/EP2016/071165 filed Sep. 8, 2016, which claims priority to German Application No. 10 2015 218 653.9 filed Sep. 28, 2015, the disclosures of which are incorporated in their entirety by reference herein.

BACKGROUND OF THE INVENTION

1. Field of the Invention

The invention relates to an electrolyte which comprises aprotic solvent, lithium-containing conducting salt, vinylene carbonate and cyclic phosphonamide, and also to a lithium-ion battery.

2. Description of the Related Art

Lithium-ion batteries are among the most promising systems for mobile applications. The fields of use range from high-value electronic equipment through to batteries for electrically driven motor vehicles.

Stock electrolyte solutions for lithium-ion batteries based on cyclic/aliphatic carbonates have been widely described and as main components form the basis of the majority of base electrolyte compositions. Vinylene carbonate (VC), which as a film-forming additive is intended to support the construction of the solid electrolyte interphase (SEI), is typically added in amounts of 2-10 wt %. U.S. Pat. No. 7,476,469 also describes stock solutions having a higher VC fraction for an anode material consisting of thin amorphous/microcrystalline silicon layers. WO15078789 describes silylated, cyclic phosphonamides and their use as additives for electrolyte mixtures in lithium-ion batteries.

On account of severe expansion in volume by Si-containing anode materials during cycling, the cycling stability of Li-ion batteries comprising Si-containing anode materials is still inadequate. The SEI layer which is formed in the initial cycles as a result of electrochemical decomposition of individual electrolyte constituents does not withstand the severe mechanical loads. Progressive reformation of the SEI layer leads to the depletion/consumption of individual electrolyte constituents and hence to a continuous decrease in the capacity of the cell as the number of cycles goes up.

SUMMARY OF THE INVENTION

A subject of the invention is an electrolyte which comprises 100 parts by weight of aprotic solvent, 1 to 50 parts by weight of lithium-containing conducting salt, 4 to 50 parts by weight of vinylene carbonate, and cyclic phosphonamide of the general formula 1

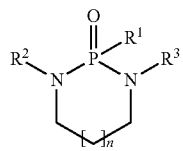

in which $R^1$, $R^2$, $R^3$ are each hydrocarbyl radicals which are unsubstituted or substituted by fluoro, chloro or silyl groups and which have 1-20 carbon atoms, where two or three of the radicals $R^1$, $R^2$, $R^3$ may be joined to one another, and n has a value of 0, 1, 2, 3, 4 or 5.

DETAILED DESCRIPTION OF THE PREFERRED EMBODIMENTS

It has been surprisingly found that the capacity retention of lithium-ion batteries during cycling can be improved significantly through the use of phosphonamides of the general formula 1 as additives in VC-rich stock electrolyte solutions. The continuous retention of capacity is in fact better than for the selected reference electrolyte mixture, starting from electrolyte compositions known from the literature for Si-containing anodes [Kawashima, A. et al., Journal of The Electrochemical Society 2011, 158, A798-A801; Aurbach, D. et al., Langmuir 2012, 28, 965-976]. The reference electrolyte mixture consists of ethyl methyl carbonate (EMC) and fluoroethylene carbonate (FEC) with a small fraction of VC.

Examples of radicals $R^1$, $R^2$, $R^3$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as the o-, m- and p-tolyl radicals, xylyl radicals and ethylphenyl radicals; and aralkyl radicals such as the benzyl radical, and the α- and the β-phenylethyl radicals.

Examples of substituted radicals $R^1$, $R^2$ and $R^3$ are the trifluoromethyl radical, the 3,3,3-trifluoro-n-propyl radical, the 2,2,2,2',2',2'-hexafluoroisopropyl radical, the 5,5,5,4,4,3,3-heptafluoropentyl radical and heptafluoroisopropyl radical, and the haloaryl radicals such as the o-, m- and p-chlorophenyl radicals, and trimethylsilylalkyl radicals having 1-6 carbon atoms in the alkyl radical, especially the trimethylsilylmethyl radical.

Preferred hydrocarbyls $R^1$ have 1-10 carbon atoms. Particularly preferred are alkyl radicals having 1 to 6 carbon atoms and alkenyl radicals having 2 to 6 carbon atoms. Especially preferred for $R^1$, $R^2$ and $R^3$ in each case are the methyl, ethyl, n-propyl, isopropyl and vinyl radicals.

If two or three of the radicals $R^1$, $R^2$ and $R^3$ are joined to one another, they may form a mono- or bicyclic hydrocarbon ring.

Preferably, n has values of 0 or 1.

Particularly preferred is N,N'-bis(trimethylsilylmethyl)-N,N'-trimethylenemethylphosphonic diamide.

The preparation of the cyclic phosphonamides of the general formula 1 is known from WO15078789.

The electrolyte preferably comprises 0.1 to 10 parts by weight, more preferably 0.5 to 5 parts by weight, and most preferably 1 to 3 parts by weight of cyclic phosphonamide of the general formula 1.

The aprotic solvent is preferably selected from organic carbonates such as dimethyl carbonate, diethyl carbonate, ethyl methyl carbonate, ethylene carbonate, vinylene carbonate, propylene carbonate, and butylene carbonate; cyclic and linear esters such as methyl acetate, ethyl acetate, butyl acetate, propyl propionate, ethyl butyrate, and ethyl isobutyrate; cyclic and linear ethers such as 2-methyltetrahydrofuran, 1,2-diethoxymethane, THF, dioxane, 1,3-dioxolane, diisopropyl ether, and diethylene glycol dimethyl ether; ketones such as cyclopentanone, diisopropyl ketone, and methyl isobutyl ketone; lactones such as γ-butyrolactone; sulfolanes; dimethyl sulfoxide; formamide; dimethylformamide; 3-methyl-1,3-oxazolidin-2-one, and mixtures of these solvents.

Particularly preferred are the above-described organic carbonates.

The electrolyte comprises preferably 5 to 40 parts by weight, more preferably 10 to 20 parts by weight, of lithium-containing conducting salt.

The lithium-containing conducting salt is preferably selected from $LiPF_6$, $LiBF_4$, $LiClO_4$, $LiAsF_6$, $(LiB(C_2O_4)_2$, $LiBF_2(C_2O_4))$, $LiSO_3C_xF_{2x+1}$, $LiN(SO_2C_xF_{2x+1})_2$ and $LiC(SO_2C_xF_{2x+1})_3$, where x adopts integral values from 0 to 8, and mixtures thereof.

The electrolytes may, as described in DE10027626A for example, also comprise further additives, such as organic isocyanates to lower the water content, HF scavengers, solubilizers for LiF, organic lithium salts and/or complex salts.

A further subject of the invention is a lithium-ion battery which comprises cathode, anode, separator and electrolyte as described above.

The negative electrode of the lithium-ion battery (anode) preferably comprises a material which is able reversibly to take on lithium ions and give them up again, such as, for example, metallic lithium, carbon, such as carbon black or graphite, silicon, tin, aluminum or lead, preferably graphite and/or silicon. The positive electrode of the lithium-ion battery (cathode) preferably comprises a lithium transition-metal oxide or a lithium transition-metal phosphate. Preferred transition metals are Ti, V, Cr, Mn, Co, Fe, Ni, Mo, W. Preferred lithium transition-metal oxides are $LiCoO_2$, $LiNiO_2$, $LiMnO_2$, $LiMn_2O_4$, $Li(CoNi)O_2$, $Li(CoV)O_2$, $Li(CoFe)O_2$. Preferred lithium transition-metal phosphates are $LiCoPO_4$, $Li(NiMn)O_2$ and $LiNiPO_4$. The electrodes of the lithium-ion battery may comprise further additives, which, for example, raise the conductivity, binders, dispersants and fillers. It is possible to use the further additives which are described in EP785586A.

Likewise, a subject of the invention is the use of the above-described electrolyte in a lithium-ion battery.

All above symbols in the above formulae have their definitions in each case independently of one another. In all formulae the silicon atom is tetravalent.

In the examples below, unless indicated otherwise in each case, all quantitative and percentage data are based on the weight, all pressures are 0.10 MPa (abs.) and all temperatures are 20° C.

EXAMPLES

1. Reference Electrolyte Mixture with ethyl methyl carbonate (EMC) and fluoroethylene carbonate (FEC) (Not Inventive)

Starting from electrolyte compositions known from the literature [Kawashima, A. et al., Journal of The Electrochemical Society 2011, 158, A798-A801; Aurbach, D. et al., Langmuir 2012, 28, 965-976], a mixture was prepared analogously of FEC/EMC in a volume ratio of 30:70. 2 wt % of vinylene carbonate and 1 M $LiPF_6$ were dissolved in this mixture.

2. Electrolyte Mixture with N,N'-bis(trimethylsilylmethyl)-N,N'-trimethylenemethylphosphonic Diamide (cyPPA)

A mixture was prepared of vinylene carbonate/ethyl methyl carbonate in a volume ratio of 12:88.

2 wt % of cyPPA and 1 M $LiPF_6$ were dissolved in this mixture.

Electrodes and cell construction used: The electrolyte mixtures from examples 1 and 2 were used to construct full cells (of type CR2032) with Si/graphite anode and NMC (nickel manganese cobalt). The quantity of electrolyte was constant at 80 μl. GF Type D Glass Microfiber Filters (Whatman) were used as a separator. The anode used consisted of 20% of silicon (unaggregated particles having an average particle size of ~180 nm), 60% of graphite (SFG 6), 8% of binder (CMC 1380) and 12% of conductive carbon black (Super P). The cathode used was a standard material consisting of 94% NMC111, 2% binder and 4% conductive material. The capacity ratio of cathode to anode that was used was 2.0/2.1 $mAh/cm^2$. The cells constructed were measured in each case for their discharge capacities in the first cycle, C1, and also for their capacity retention after 100 (retention C100) and 300 (retention C300) cycles. The results are set out in table 1.

Apparatus and measurement methods: Electrochemical testing took place on a BaSyTeC CTS-Lab Battery Test System test stand in full-cell button cells. The cells were first formed in the voltage window of 4.2-3.0 V in two cycles at C/10 and with a subsequent CV step in each case (4.2 V to 3 V, C/10, cccv (cv step to I<0.01 CA)). Subsequently, in the same voltage window, 300 cycles were run at C/2 with a subsequent CV step in each case (4.2 V to 3 V, C/2, cccv (cv step to I<0.125 CA)).

TABLE 1

| Electrolyte mixture | Discharge capacity C1 [$mAh/cm^2$] | Retention C100 [%] | Retention C300 [%] |
| --- | --- | --- | --- |
| 1 not inventive | 1.80 | 63.1 | 46.4 |
| 2 with cyPPA | 1.74 | 80.5 | 68.0 |

The effect of the cyclic phosphonamide of the general formula 1 is evident from the capacity retention in table 1: an improvement of around 17% after 100 cycles and an improvement of around 22% after 300 cycles is achieved relative to the reference electrolyte mixture (see example 1).

The same initial state (charging, balancing) of the electrodes in the cells comprising electrolyte mixtures 1 and 2 is verified by approximately equal discharge capacity of the cells in the first cycle C1.

The invention claimed is:

1. An electrolyte, comprising:
   100 parts by weight of at least one aprotic solvent,
   1 to 50 parts by weight of at least one lithium-containing conducting salt,
   4 to 50 parts by weight of vinylene carbonate, and
   at least one cyclic phosphonamide of the formula 1

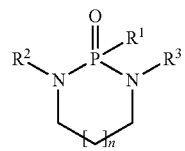

in which
$R^1$, $R^2$, $R^3$ are each independently hydrocarbyl radicals which are unsubstituted or substituted by fluoro, chloro or silyl groups and which have 1-20 carbon atoms, where two or three of the radicals $R^1$, $R^2$, $R^3$ may be joined to one another, and
n has a value of 0, 1, 2, 3, 4 or 5.

2. The electrolyte of claim 1, wherein $R^2$ and $R^3$ are trimethylsilylalkyl radicals having 1-6 carbon atoms in the alkyl radical.

3. The electrolyte of claim 2, wherein $R^1$ is an alkyl radical having 1 to 6 carbon atoms.

4. The electrolyte of claim 2, wherein n has a value of 1.

5. The electrolyte of claim 1, wherein $R^1$ is an alkyl radical having 1 to 6 carbon atoms.

6. The electrolyte of claim 5, wherein n has a value of 1.

7. The electrolyte of claim 1, wherein n has a value of 1.

8. The electrolyte of claim 1, wherein the electrolyte comprises 0.1 to 10 parts by weight of cyclic phosphonamide(s) of the formula 1.

9. The electrolyte of claim 1, wherein at least one aprotic solvent is selected from the group consisting of organic carbonates, cyclic and linear esters, cyclic and linear ethers, ketones, lactones, sulfolanes, dimethyl sulfoxide, formamide, dimethylformamide, 3-methyl-1,3-oxazolidine-2-one and mixtures of these solvents.

10. The electrolyte of claim 1, wherein at least one lithium-containing conducting salt is selected from the group consisting of $LiPF_6$, $LiBF_4$, $LiClO_4$, $LiAsF_6$, $LiSO_3C_xF_{2x+1}$, $(LiB(C_2O_4)_2$, $LiBF_2(C_2O_4))$, $LiN(SO_2C_xF_{2x+1})_2$ and $LiC(SO_2C_xF_{2x+1})_3$, where x adopts integral values from 0 to 8, and mixtures thereof.

11. The electrolyte of claim 1, which comprises 0.1-10 wt % of cyclic phosphonamide(s) of the formula 1.

12. A lithium-ion battery, comprising: a cathode, an anode, a separator, and an electrolyte of claim 1.

13. The lithium-ion battery of claim 12, wherein the anode is a silicon-containing anode.

* * * * *